United States Patent
Nagaki et al.

(10) Patent No.: US 9,139,861 B2
(45) Date of Patent: Sep. 22, 2015

(54) CULTURE SUBSTRATE COMPRISING CELLULOSE GEL, SOLID MEDIUM USING SAME, AND CELLULASE ACTIVITY ASSAY METHOD USING MEDIUM

(75) Inventors: Kazunori Nagaki, Ibaraki (JP); Yasunori Kurosawa, Ibaraki (JP); Takuo Shiraishi, Ibaraki (JP); Shigeru Deguchi, Kanagawa (JP); Mikiko Tsudome, Kanagawa (JP)

(73) Assignees: Japan Agency for Marine-Earth Science and Technology, Kanagawa (JP); Kyokuto Pharmaceutical Industrial Co., Ltd., Tokyo (JP)

( * ) Notice: Subject to any disclaimer, the term of this patent is extended or adjusted under 35 U.S.C. 154(b) by 0 days.

(21) Appl. No.: 13/881,756

(22) PCT Filed: Oct. 24, 2011

(86) PCT No.: PCT/JP2011/074410
§ 371 (c)(1),
(2), (4) Date: Apr. 26, 2013

(87) PCT Pub. No.: WO2012/057064
PCT Pub. Date: May 3, 2012

(65) Prior Publication Data
US 2013/0323768 A1    Dec. 5, 2013

(30) Foreign Application Priority Data
Oct. 29, 2010 (JP) .................................. 2010-244327

(51) Int. Cl.
*C12Q 1/34* (2006.01)
*C12N 1/22* (2006.01)
*C12Q 1/04* (2006.01)

(52) U.S. Cl.
CPC .. *C12Q 1/34* (2013.01); *C12N 1/22* (2013.01); *C12Q 1/045* (2013.01); *C12N 2533/78* (2013.01); *G01N 2333/942* (2013.01)

(58) Field of Classification Search
None
See application file for complete search history.

(56) References Cited

U.S. PATENT DOCUMENTS
2007/0172938 A1    7/2007  Deguchi et al.

FOREIGN PATENT DOCUMENTS
WO    2005/083056 A1    9/2005

OTHER PUBLICATIONS

Matsumoto et al., Solution properties of celluloses from different biological origins in LiCl-DMAc, Cellulose, 00: pp. 1-8, 2002.*
International Search Report issued in PCT/JP2011/074410 mailed on Dec. 6, 2011 (2 pages).
Deguchi, S. et al.; "Preparation and characterisation of nanofibrous cellulose plate as a new solid support for microbial culture"; Soft Matter, The Royal Society of Chemistry 2007, vol. 3, No. 9, , pp. 1170-1175 (6 pages).

* cited by examiner

*Primary Examiner* — Karen Cochrane Carlson
*Assistant Examiner* — Jennifer M. H. Tichy
(74) *Attorney, Agent, or Firm* — Osha Liang LLP

(57) ABSTRACT

A cellulose gel medium having good visibility of microbial colonies, a cellulose gel culture substrate for manufacturing the cellulose gel medium, a method for manufacturing the cellulose gel culture substrate, a method for screening cellulase-producing microorganisms or cellulase activity with greater efficiency and rapidity, and a culture substrate, which includes a cellulose gel containing cellulose and water as medium-solidifying components, the cellulose has the viscosity of 12 to 35 mPa·S as measured at 26° C. with a solution prepared by dissolving the cellulose at a concentration of 2.5 mg/mL in dimethylacetamide containing 8% (W/V) lithium chloride.

16 Claims, 16 Drawing Sheets

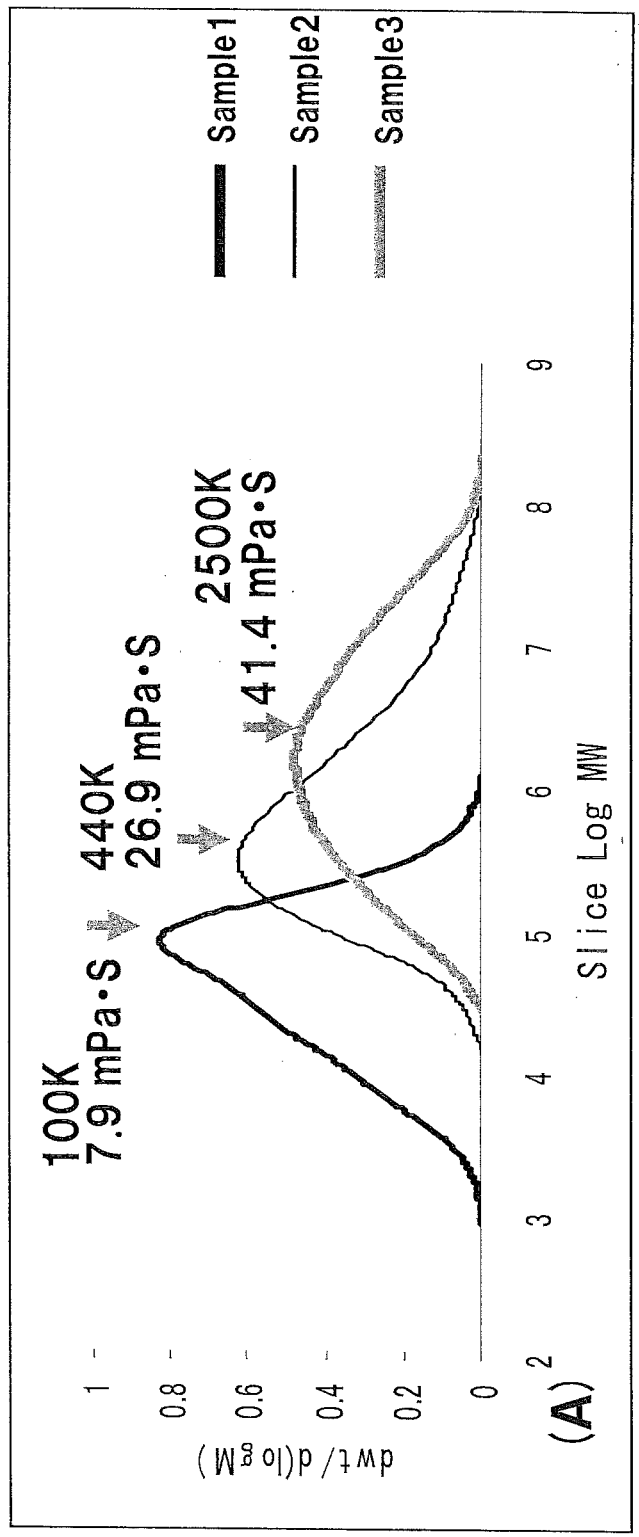
Fig 1-A

Fig 1-B
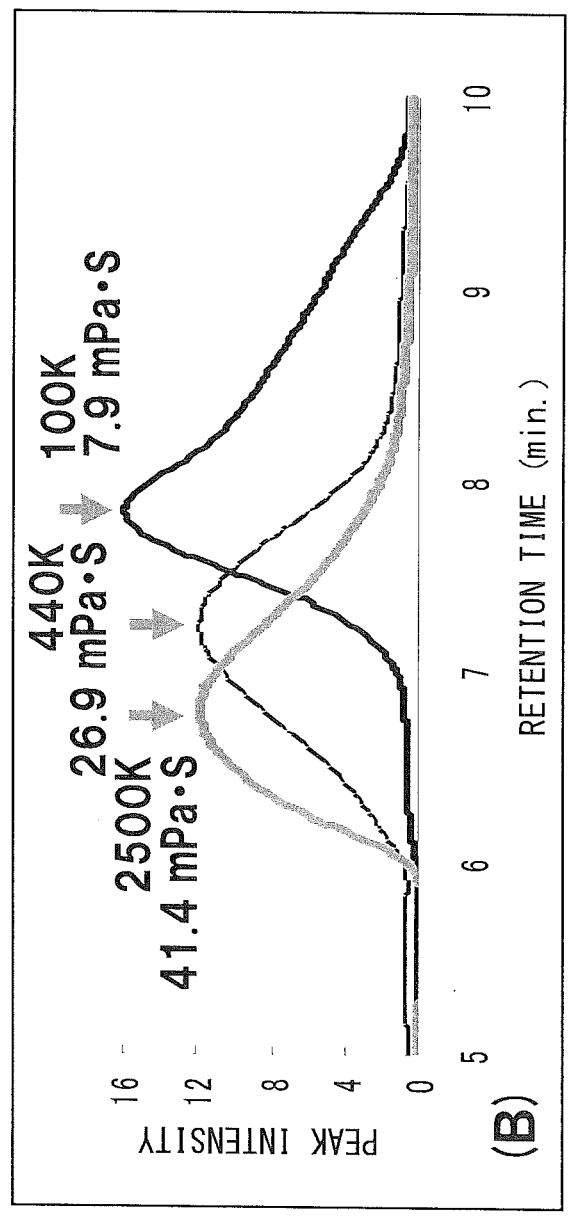

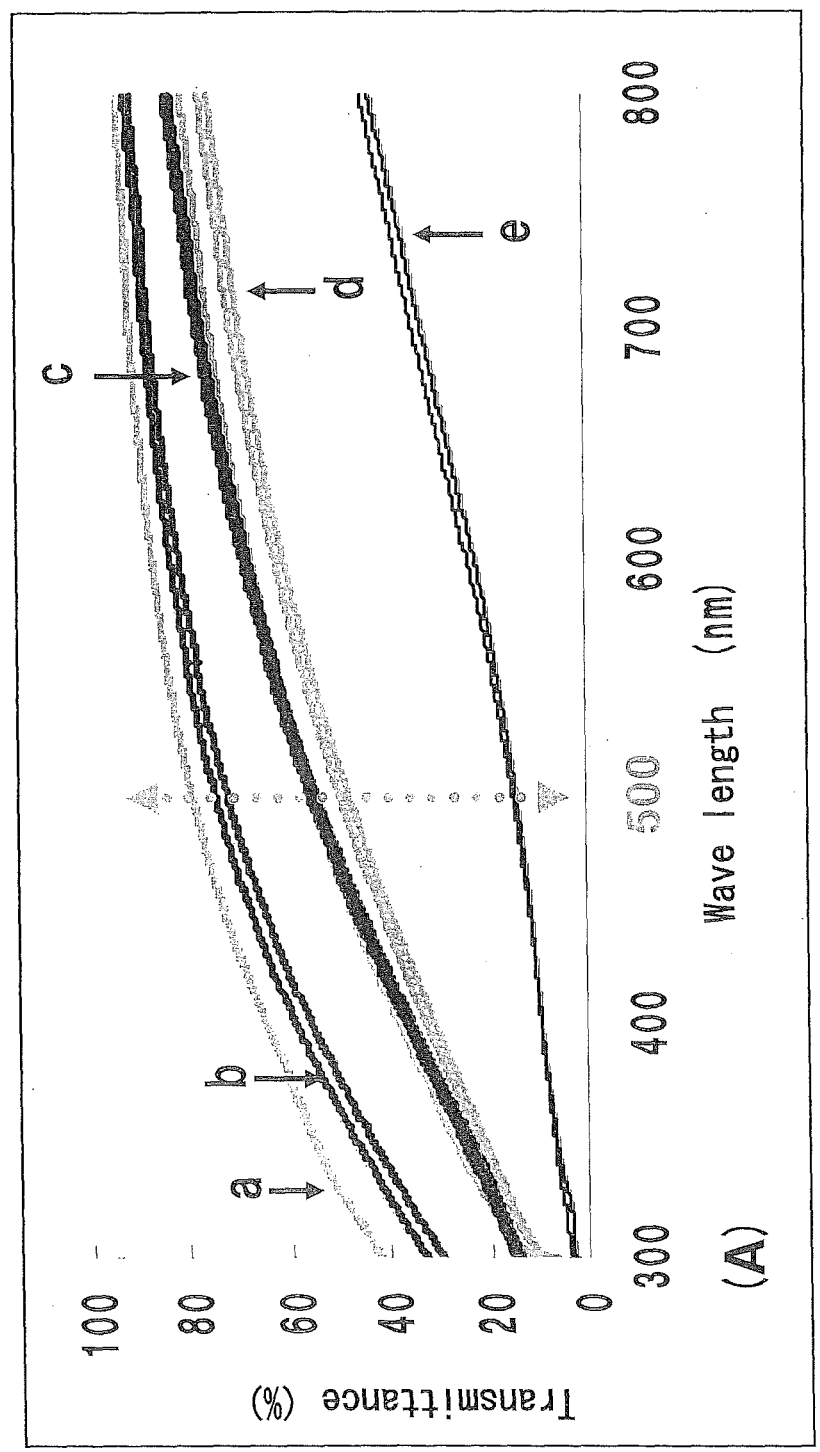
Fig 4-A

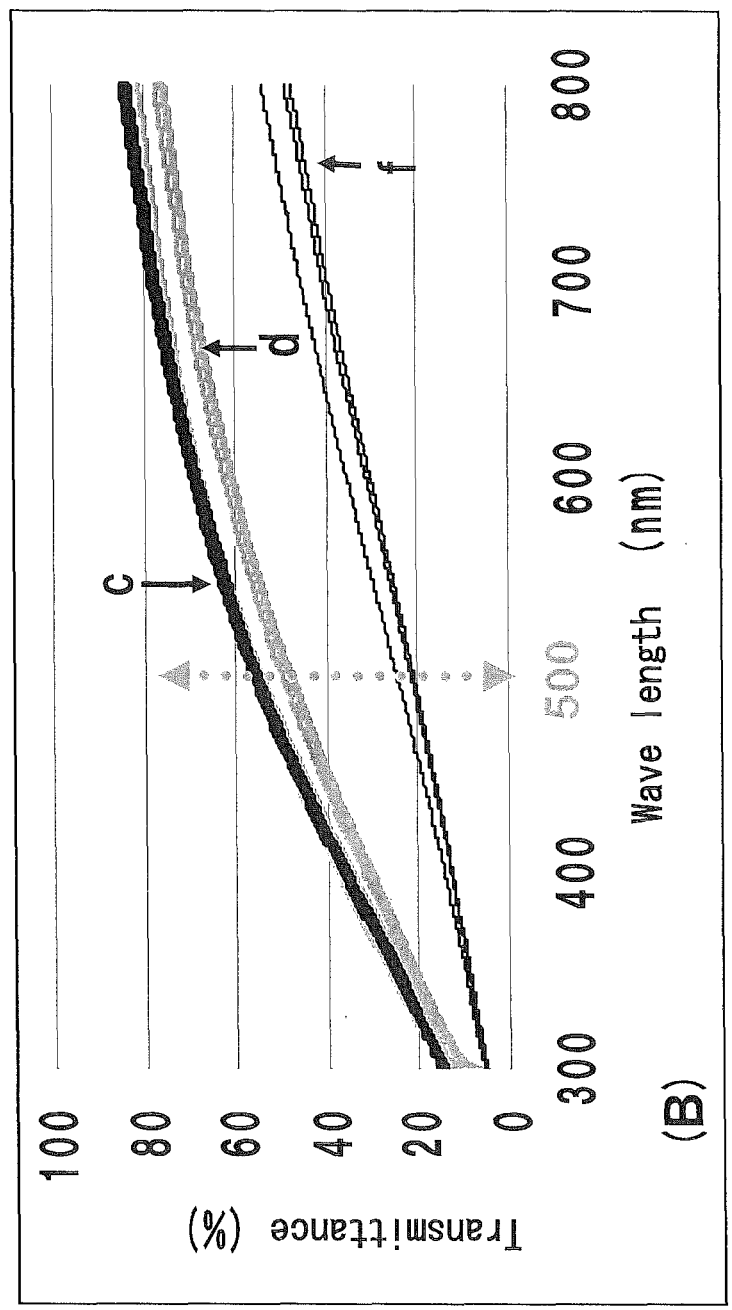
Fig 4-B

|  | Diameter (cm) | Gel thickness (mm) | Density (mg/cm3) | Relative volume (%) |
|---|---|---|---|---|
| Sample1 1% | 8.4 | 1.95 | 13.9 | 100 |
| Sample2 1% | 8.2 | 1.90 | 15.0 | 93 |
| Sample3 1% | 6.6 | 1.93 | 22.5 | 61 |

FIG. 12

|  | Force required to break the gel | Distance when the gel broke |
|---|---|---|
| 3% Sample1 | 2.48±0.33 N | 2.70±0.31 mm |
| 1% Sample2 | 1.22±0.17 N | 5.95±0.60 mm |

FIG. 13

| Sample2 | Treatment time | Peak top MW | Viscosity (mPa·S) | Transmittance (500 nm) | Max. stress (N) | Density (mg/cm3) |
|---|---|---|---|---|---|---|
| | 0 | 451000 | 26.9 | 39.2 | 0.35 | 13.8 |
| | 5 | 273000 | 22.1 | 39.9 | 0.36 | 13.9 |
| | 18 | 199000 | 16.1 | 37.0 | 0.29 | 13.3 |
| | 30 | 142000 | 15.5 | 34.5 | 0.21 | 12.5 |
| | 43 | 117000 | 13.3 | 36.8 | 0.20 | 11.7 |
| | 91 | 37000 | 5.58 | 26.1 | 0.04 | 10.4 |

FIG. 14

| Sample3 | Treatment time | Peak top MW | Viscosity (mPa·S) | Transmittance (500 nm) | Max. stress (N) | Density (mg/cm3) |
|---|---|---|---|---|---|---|
| | 0 | 2540000 | 41.37 | 18.9 | 0.36 | 20.3 |
| | 5 | 1890000 | 36.84 | 21.7 | 0.26 | 19.2 |
| | 18 | 1090000 | 32.81 | 27.9 | 0.16 | 15.1 |
| | 30 | 174000 | 17.34 | 36.1 | 0.15 | 12.8 |
| | 43 | 110000 | 9.58 | 30.6 | 0.08 | 11.1 |

FIG. 15

CULTURE SUBSTRATE COMPRISING CELLULOSE GEL, SOLID MEDIUM USING SAME, AND CELLULASE ACTIVITY ASSAY METHOD USING MEDIUM

CROSS REFERENCE TO RELATED APPLICATIONS

This is a national stage application of PCT/JP2011/074410, filed on Oct. 24, 2011, which claims priority to Japanese Patent Application No. 2010-244327, filed on Oct. 29, 2010. This application claims the benefits of these prior filed applications and incorporates the disclosures of these prior filed applications by reference in their entirety.

TECHNICAL FIELD

The present invention relates to a culture substrate for producing a solid medium that is used for the culture of microorganisms and the like, a solid medium using this culture substrate, and a method for producing the culture substrate.

BACKGROUND ART

In the method for solid culture of microorganisms and the like, solid media using agar or agarose as a solidifying agent have been conventionally used. This is because there are advantages such as those that production is easy, cultured microorganisms can be easily discriminated by visual inspection, and isolation of microorganisms can be easily carried out. However, these solid media are such that the gel is dissolved in a severe environment of high temperature, extreme pH, and the like, therefore the microorganisms that can be cultured are limited.

In order to enable culture of microorganisms in such an extreme environment, a cellulose gel medium which employs cellulose only as a solidifying agent has been developed. For example, Patent Document 1 (WO 2005/083056) describes a solid medium containing, as a medium solidifying component, a cellulose gel which is a porous cellulose gel structure having a backbone moiety composed of cellulose and having a cellulose concentration of 0.01% or greater and a porosity of 50% or greater, and a method for the production thereof. This solid medium of the invention is produced by dispersing cellulose in a solvent (particularly, an aqueous thiocyanate solution), dissolving cellulose therein under stirring and/or heating, subsequently gelling the solution by cooling and/or solvent removal to obtain a cellulose gel, and causing nutrients to penetrate into the cellulose gel. Since this cellulose gel is produced by using unmodified cellulose as a raw material, the cellulose gel exhibits strong resistance even to heat, extreme pH, high salt concentrations, solubility in water or organic solvents, and the like. Accordingly, the cellulose gel medium thus produced is such that the gel does not dissolve even in an environment called an "extreme environment" in the field of microbial culture. Therefore, it is described that this medium can be used under a wider range of culture conditions in which a conventional solid medium such as an agar medium cannot be used.

As such, solid media that use cellulose gel have an excellent advantage that culture can be carried out without softening or syneresis even under the conditions in which culture is difficult in a solid medium using agarose gel, gellan gum or silica gel, for example, at a high temperature of 100° C. or under strongly acidic or strongly alkaline conditions. However, it is described in Non-Patent Document 1 (Deguchi et al., Soft Matter, (2007), 3, 1170-1175) that in order to produce a cellulose gel medium which is appropriate for microbial culture, the optimal cellulose concentration is 2% to 3% by weight, and if the concentration is less than 1% by weight, the gel loses its physical strength and becomes very brittle, so that it is difficult to apply or disperse microorganisms thereon. Furthermore, it is described that if the cellulose concentration is greater than 3% by weight, the medium surface after solidification does not become flat, and inoculation of microorganisms cannot be achieved. Therefore, production of cellulose gel media for microbial culture is highly limited under the current circumstances.

Furthermore, a cellulose gel having a cellulose concentration which is suitable as a solid medium in view of physical strength or smoothness, such as described above, does not have such transparency as that of agar or agarose gel media and is white in color. Since most of the microbial colonies are whitish, visibility of the colonies on cellulose gel media is poor, and cellulose gel media are not suitable for the observation of colonies. However, there has been no alternative to improve this situation.

Cellulose gel media are also useful for the screening of cellulase-producing bacteria. Conventionally, the screening of cellulase-producing bacteria has been carried out by a method of using carboxymethyl cellulose (CMC) or the like, but as a result of the use of cellulose gel media, the screening efficiency has dramatically improved as compared with conventional methods. This improvement is based on the reason that since cellulose, which is the material of cellulose gel media, is a direct substrate of cellulases, when cellulose is decomposed, the presence of cellulase-producing bacteria at the place of decomposition can be visually determined, and therefore, a separate operation for confirming the cellulase activity is not required, and that production of replicas for screening is not required.

In regard to screening, since an increase in the efficiency of operation, particularly shortening of the detection time, greatly affects the development status thereafter, a speedup of screening has been constantly desirable. Decomposition of cellulose gel by a cellulase is such that the influence of the decomposition can be more clearly observed as the cellulose density is lower. However, in the current situation, since it has been difficult to reduce the cellulose concentration in the cellulose gel, further speedup could not be desired. Furthermore, since cellulose media are white in color, checking of holes produced by decomposition has been difficult in the early stage of culture.

CITATION LIST

Patent Document

Patent Document 1: WO 2005/083056 A (Title of the Invention: "Solid cellulosic culture medium and process for producing the same")

Non-Patent Document

Non-Patent Document 1: Deguchi et al., Preparation and characterization of nanofibrous cellulose plate as a new solid support for microbial culture. Soft Matter, (2007), 3, p. 1170-1175

DISCLOSURE OF INVENTION

Problem to be Solved by the Invention

An object of the present invention is to provide a cellulose gel culture substrate for producing a cellulose gel medium which provides good visibility for microbial colonies, by improving the defects of conventional cellulose gel media such as described above, and a method for producing the culture substrate. Another object of the present invention is to provide a solid medium using this culture substrate. Still another object of the present invention is to provide a method for screening a cellulase-producing microorganism or cellulase activity more rapidly and more efficiently.

Means for Solving Problem

The present invention provides:

[1] a culture substrate formed of a cellulose gel including cellulose as a medium solidifying component and water, the cellulose having a viscosity of 12 mPa·S to 35 mPa·S as measured at 26° C. with a solution prepared by dissolving the cellulose in dimethylacetamide including 8% (W/V) lithium chloride at a concentration of 2.5 mg/mL;

[2] the culture substrate according to the item [1], wherein the light transmittance of the cellulose gel having a thickness of 2 mm at a wavelength of 500 nm is 25% or greater;

[3] the culture substrate according to the item [1] or [2], wherein the peak top molecular weight of the cellulose obtainable by gel filtration is 115,000 to 1,100,000;

[4] the culture substrate according to any one of the items [1] to [3], wherein the culture substrate is accommodated in a container;

[5] a solid medium formed of the culture substrate according to any one of the items [1] to [4], wherein the cellulose gel includes a nutrient component;

[6] a method for producing a cellulose gel culture substrate, the method comprising dispersing in water cellulose having a viscosity of 12 mPa·S to 35 mPa·S as measured at 26° C. with a solution prepared by dissolving the cellulose in dimethylacetamide including 8% (W/V) lithium chloride at a concentration of 2.5 mg/mL, adding a solid thiocyanate, subsequently heating and dissolving the cellulose, and solidifying the solution by lowering the temperature; and

[7] an assay method for the cellulase production by a test microorganism or the cellulase activity of a test specimen, the method comprising bringing the solid medium according to the item [5] into contact with the test microorganism or the test specimen, and determining the presence or absence, or the degree of dissolution of a cellulose gel.

Effect of the Invention

Since the cellulose gel culture substrate of the present invention and a solid medium using the substrate have transparency (light transmittance) to the same extent as that of agar media, visibility of colonies on cellulose gel media, which is a defect of the conventional gel media, is improved dramatically, and determination of colonies can be easily carried out. Furthermore, in spite of the low cellulose concentration and the low density of the gel, the cellulose gel culture substrate of the present invention and a solid medium using the substrate maintain all of those advantageous features possessed by conventional cellulose gel media, such as being physically strong and difficult to dissolve. Therefore, the cellulose gel culture substrate and the solid medium can be used for the solid culture of various microorganisms in a severe environment, similarly to the conventional cellulose gel media.

Furthermore, in regard to the screening of microorganisms, it is desirable to carry out the operation of isolating an intended microorganism rapidly and accurately. By using the cellulose gel culture substrate of the present invention and a solid medium using the substrate, screening in a shorter time is enabled. That is, the cellulose gel culture substrate of the present invention and a solid medium using the substrate do not require production of replicas or a separate assay of cellulase activity, and the presence or absence, or the intensity of the cellulase activity of an isolated microorganism or the activity of a recombinant cellulase can be directly evaluated by visual inspection on the medium. Furthermore, since the cellulose gel culture substrate of the present invention and a solid medium using the substrate have a gel density of about 1/7 to 1/2 of the gel densities of conventional cellulose gel media, the configuration of the decomposition of cellulase (cellulase activity) can be judged easily and rapidly in a very short time. Therefore, according to the present invention, the efficiency of the operation of searching for a cellulose-decomposing microorganism or determining the intensity of the enzyme activity can be enhanced.

Furthermore, in regard to the cellulose gel culture substrate of the present invention and a solid medium using the substrate, since the selection range of the cellulose raw material is broad, the cellulose substrate and the solid medium can have any arbitrary strength and can be used in, for example, plant callus culture in addition to the microbial culture application.

BRIEF DESCRIPTION OF DRAWINGS

FIG. 1 is diagrams illustrating the results of the molecular weight measurement of various celluloses based on gel filtration. Panel (A) is a diagram illustrating the molecular weight distributions and peak top molecular weights of various cellulose samples calculated from a calibration curve; and panel (B) is a diagram illustrating the patterns of gel filtration obtained by injecting various samples. The bold black line represents sample 1, the fine black line represents sample 2, and the bold grey line represents sample 3. The arrows represent the positions of the peak top molecular weights of various samples;

FIG. 4 is diagrams illustrating the light transmittances of various culture substrates. Panel (A) illustrates the transmittances of culture substrates produced by using 1% agar, sample 1 (1% and 3%), and sample 2 (0.5% and 1%), respectively. Panel (B) illustrates the transmittances of culture substrates produced by using samples 1 to 3 (all 1%), respectively. The line of "a" represents 1% agar (Comparative Example), the line of "b" represents sample 2 (0.5%), the line of "c" represents sample 2 (1%), the line of "d" represents sample 1 (1%), the line of "e" represents sample 1 (3%), and the line of "f" represents sample 3 (1%) (n=3);

FIG. 12 shows characteristics of samples 1, 2, and 3.

FIG. 13 shows tensile strengths of samples 1 and 2.

FIG. 14 shows characteristics of sample 2 at different treatment times.

FIG. 15 shows characteristics of sample 3 at different treatment times.

BEST MODE(S) FOR CARRYING OUT THE INVENTION

Figure 2:
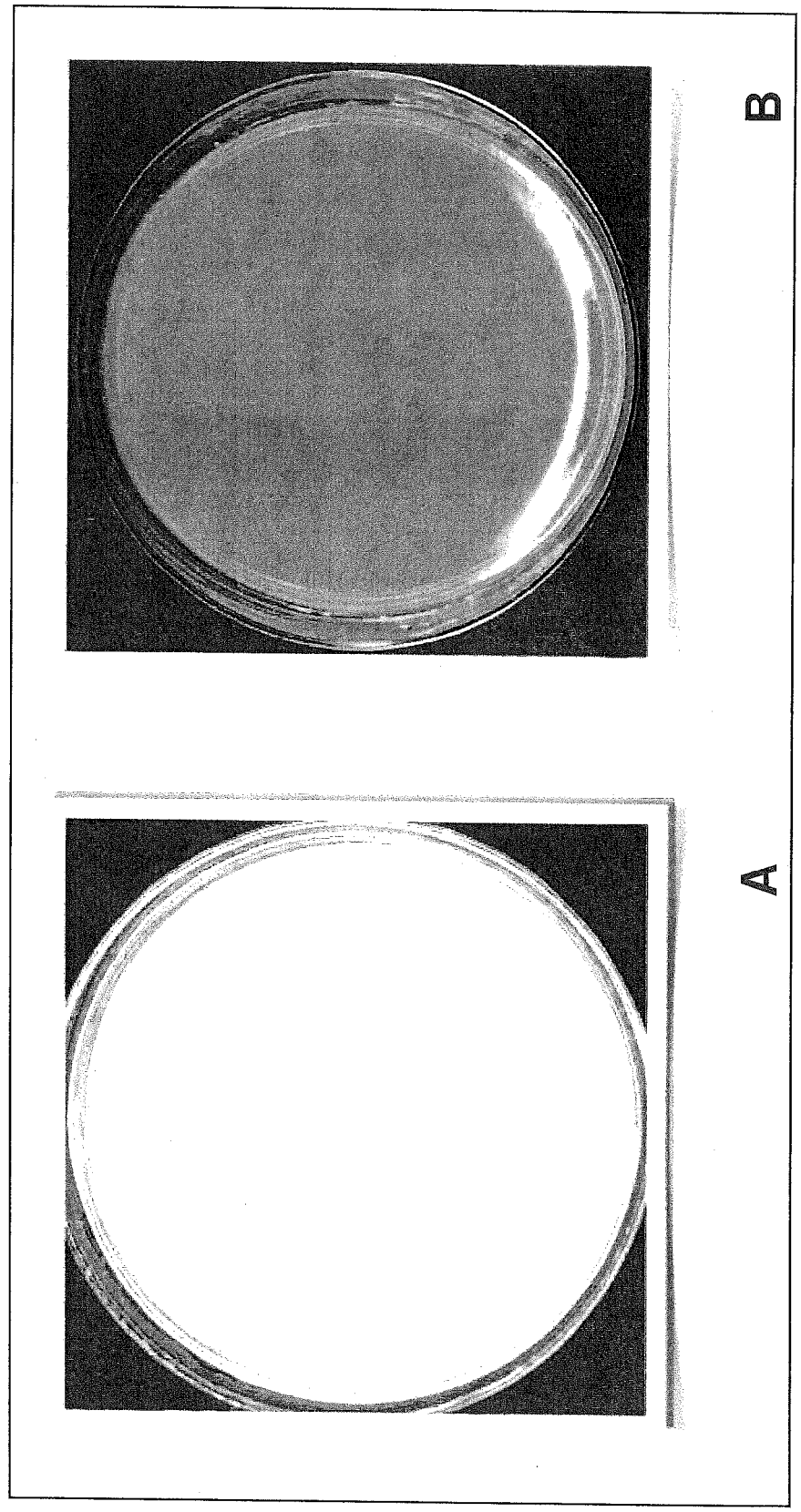
FIG. 2 is photographs of various culture substrates taken with a digital camera from above. Panel (A) illustrates a culture substrate produced by using sample 1 (cellulose concentration: 3%); and panel (B) illustrates a culture substrate produced by using sample 2 (cellulose concentration: 1%)

In regard to conventional cellulose gel media, it has been believed that the optimum cellulose concentration is 2% to 3%, and if the cellulose concentration is reduced, physical strength is not retained, and the cellulose gel media may not be suitable for the use as a culture medium. Regarding polymer compounds, since the viscosity increases as the molecular weight increases, from the viewpoint of increasing the physical strength, use of cellulose having a large molecular weight, for example, bacterial cellulose, may be considered. However, in contrast to the expectation, the inventors of the present invention found that a cellulose gel which uses such cellulose having a large molecular weight at a low concentration undergoes unpredictable irregular shrinkage, and thus a uniform medium cannot be produced and the cellulose gel is not suitable for use, and that by using cellulose having certain particular properties, a cellulose gel having sufficient strength even at a low concentration can be produced. Thus, the inventors completed the invention.

That is, the cellulose that is used in the present invention may be microorganism-derived cellulose or plant-derived cellulose, but plant-derived cellulose is preferred. The molecular weight (peak top molecular weight) obtainable by gel filtration may be 115,000 to 1,100,000, and is preferably 115,000 to 550,000. The cellulose used in the present invention is such that the viscosity at 26° C. of a solution prepared by dissolving the cellulose in dimethylacetamide containing 8% (W/V) lithium chloride at a concentration of 2.5 mg/mL, is preferably 12 mPa·S to 35 mPa·S, more preferably 12 mPa·S to 30 mPa·S, and particularly preferably 12 mPa·S to 27 mPa·S.

The cellulose concentration in the cellulose gel culture substrate and medium of the present invention may be adjusted to a low concentration of about 0.1% to about 1.8%, and the cellulose concentration is preferably 0.2% to 1.5%, and most preferably 0.5% to 1%.

When the cellulose such as described above is used at the aforementioned concentration, a cellulose gel which has higher transparency as compared with conventional gels and has a transparency comparable to an agar medium, may be produced. The cellulose gel of the culture substrate and medium of the present invention is such that the total light transmittance of the cellulose gel having a thickness of 2 mm (±0.1 mm) at a wavelength of 500 nm is 25% or higher, preferably 30% or higher, and 100% at the maximum. Meanwhile, the total light transmittance is measured as described below:

cellulose gel (thickness: about 2 mm (2 mm±0.1 mm)) held in a Petri dish is measured by using a spectrophotometer ("Beckman Coulter DU800" or an equivalent instrument) in the transmittance measurement (T %) mode at a wavelength of 500 nm. The transmittance of the Petri dish holding the culture substrate is designated as a blank.

The cellulose gel culture substrate is basically formed of a cellulose gel containing water (and an accommodating container). In the cellulose gel culture substrate, if necessary, substances or solvents that dissolve in water may also be incorporated in addition to the gel described above. Examples of such arbitrary components include organic solvents that dissolve in water (for example, alcohols (methanol, ethanol, propanol and the like), and polar organic solvents such as acetone), and various constituent components of culture media, such as a pH adjusting agent and a colorant.

The cellulose gel culture substrate of the present invention may be produced according to the conventional methods described in Patent Document 1, Non-Patent Document 1, and the like, but preferably, the culture substrate may be produced as follows. Cellulose weighed to obtain a desired concentration is added to water in a required amount that has been calculated in advance, and by stirring the mixture, the cellulose is sufficiently dispersed therein. To this, solid thiocyanate is added to a concentration of 50% (W/W) or greater, the mixture is sufficiently stirred and mixed at room temperature, and then the mixture is heated and stirred to thereby dissolve the cellulose. Regarding the heating temperature, a temperature of about 90° C. to about 100° C. is an appropriate temperature, and the heating time is about 10 minutes to about 30 minutes. This solution is dispensed into a predetermined container and is solidified by cooling, and thus a cellulose gel is formed. Thereafter, the cellulose gel is sufficiently desalted, and thereby a culture substrate formed from water and a cellulose gel is obtained. For example, after solidification, the cellulose gel is subjected to an alcohol treatment and desalting. Specifically, the alcohol treatment may be carried out by adding an alcohol (ethanol, methanol or the like) in an amount equal to that of the cellulose gel (final concentration: 50% (V/V)), and shaking the mixture at room temperature for several hours. The desalting process may be carried out by, for example, washing with water.

The cellulose gel culture substrate produced as described above may be sterilized according to a known method. Regarding the sterilization method, high pressure steam sterilization (typically for about 15 to 20 minutes at 121° C.) is preferred.

Regarding the container for holding the cellulose gel, containers of arbitrary shapes and materials, such as Petri dishes of various sizes (for the production of plate media) or test tubes (for the production of slant media), may be utilized. From the viewpoint of the visibility of microorganisms, the material is preferably a transparent material or a translucent material, and transparent materials (for example, glass and plastics) are most preferred.

By incorporating a nutrient component into this culture substrate, a solid medium may be produced. The nutrient components may be incorporated into a culture substrate by, for example, adding a liquid medium (culture fluid) which is at a two-fold concentration and has the same volume as the volume of the cellulose gel, to the culture substrate, and replacing the water within the gel with the liquid medium to obtain a one-fold concentration. As the nutrient components, any components may be selected, according to the purpose of use, from various media of known formulations, or media based on those media of known formulations with arbitrary components added thereto or removed therefrom.

A wide variety of microorganisms may be cultured by using the culture substrate and medium of the present invention. These microorganisms include conventionally known bacteria, fungi, archaebacteria and the like, which can be grown under standard conditions, and in addition to them, the culture substrate and the medium may be used for the isolation of unknown microorganisms that live in a special environment such as in an extreme environment under the conditions of high temperature, extreme pH and high salt concentration, or in the presence of an organic solvent.

Cellulose that constitutes the cellulose gel is the original substrate of cellulase. Therefore, a cellulose medium has an advantage that, unlike conventional agar media or cellulose-containing agarose gel media, the decomposition activity of a cellulase may be confirmed directly by visual inspection on the medium. Since the rate of decomposition of a cellulose gel by a cellulase depends on the density of cellulose, the presence or absence of cellulase activity and the like may be easily and visually determined by using a low-density gel which uses a low concentration of cellulose. Since the cellulose gel culture substrate and medium of the present invention may use cellulose in an amount per unit volume of about $\frac{1}{7}$ to $\frac{1}{2}$ of the amount of cellulose used in conventional cellulose gel plates, decomposition of the gel by a cellulase occurs rapidly to a broad extent, and detection of cellulase activity and the intensity of the activity may also be rapidly and easily observed. Therefore, the medium of the present invention is particularly suitable for the screening of cellulase activity or its intensity, in addition to the culture of various microorganisms as described above.

An example of the screening method is as follows. For example, a NB (nutrient broth) medium or the like is used as the medium, and the medium is diluted to a concentration of about $\frac{1}{2}$ to $\frac{1}{100}$ of the conventionally used medium concentration. This medium is infiltrated into the cellulose gel culture substrate of the present invention to produce a medium for screening. Regarding the sample, for example, wood chips, stems, leaves or the like that are collected, washed with sterile water, subsequently dried on a filter paper or the like, and subjected to cutting or the like as necessary, are used as samples and are directly left to stand on the medium. Alternatively, finely cut samples are suspended in sterile water or the like, and then the suspension is applied on the medium. This medium is left to stand in an incubator, and culture is carried out at a constant temperature in a temperature range of 20° C. to 40° C. for an appropriate time period. After the culture, the size, number and the like of holes produced by dissolution of the cellulose gel are visually observed, and the results are compared with a positive control and a negative control. Thereby, cellulase activity or the presence or absence of a cellulase-producing microorganism in the samples, or the intensity of activity may be judged.

Hereinafter, the present invention will be described in more detail by way of Production Examples and Test Examples for the cellulose gel culture substrate and solid medium of the present invention. Meanwhile, in the following description, unless particularly stated otherwise, "%" represents "% (W/V)".

1. Measurement of Molecular Weight by Gel Filtration of Cellulose Sample

As cellulose samples, trade name "Avicel", manufactured by Merck GmbH ("sample 1"), trade name "Celish", manufactured by Daicel FineChem, Ltd. ("sample 2"), and bacterial cellulose (BC) ("sample 3") were used. Samples 1 and 2 were plant-derived celluloses. Meanwhile, sample 1 was equivalent as that used in the experiments described in Patent Document 1 and Non-Patent Document 1.

150 mg of each of the cellulose samples was dispersed in 100 mL of pure water, and the dispersion was stirred by shaking on a shaker (speed of rotation: 140 rpm, Takasaki Kagaku Kikai K. K.; hereinafter, the same) for 24 hours or longer at room temperature. The dispersion was subjected to suction filtering using a filter paper, and the cellulose sample thus collected was washed by redispersing the sample in 100 mL of acetone (Wako Pure Chemical Industries, Ltd.), and stirring by shaking on a shaker for 24 hours or longer at room temperature.

Next, the liquid was removed from the cellulose sample by suction filtering using a filter paper, and then the sample was washed with dimethylacetamide (DMAc, Wako Pure Chemical Industries, Ltd.). That is, the cellulose sample was redispersed in 100 mL of DMAc, and the dispersion was stirred by shaking on a shaker for 24 hours or longer at room temperature.

Liquid was removed from the cellulose sample by suction filtering using a filter paper, and then the sample was sandwiched between filter papers to remove any excess liquid. The sample was subjected to vacuum drying overnight at room temperature, DMAc containing 8% LiCl (Wako Pure Chemical Industries, Ltd.) was added to the sample to obtain a sample concentration of 10 mg/mL, and the mixture was left to stand at 40° C. until the sample dissolved. The solution was diluted 20-fold with DMAc containing 1% LiCl, and the dilution was centrifuged by using a high speed centrifuge (CF16RXII, Hitachi, Ltd.) at 15,000 rpm for 15 minutes. The supernatant was collected.

As molecular weight markers, polyethylene glycols (PEG, Kanto Chemical Co., Inc.) and polyethylene oxide (PEO, Kanto Chemical Co., Inc.) of various molecular weights were added to DMAc containing 1% LiCl such that the final concentration of each of the polymer would be 0.5 mg/mL. The sizes of the molecular weight markers were 900,000, 580,000, 270,000, 190,000, 100,000, 43,000, 21,000, 6,000, 4,000, 1,000, 600, 400, and 200. After the molecular weight markers were prepared, the markers were left to stand at 40° C. until the PEG's and PEO's dissolved. The markers were centrifuged at 15,000 rpm for 15 minutes, and the supernatants were collected.

An HPLC analysis was carried out as follows. For the analyzer model, trade name "Waters e2695" manufactured by Waters Corp. was used as the main instrument of HPLC, and trade name "Differential Refractometer 2414" manufactured by Waters Corp. was used as the detector. Columns used were two of trade name "TSKgel SuperAWM-H" (particle size: 9 μm, 60 mm I.D.×15 cm) manufactured by Tosoh Corp., and one of trade name "guard column: TSKguardcolumn SuperAW-H" (4.6 mm I.D.×3.5 cm) manufactured by Tosoh Corp. The flow rate was set to 0.6 mL/min, and DMAc containing 1% LiCl was used as the eluent. The amount of sample injection was 50 μL, and the column temperature was set at 40° C. The differential refractometer was set to positive (+) and Res (1 s).

The results are presented in FIG. 1. Panel (A) illustrates the molecular weight distributions and the peak top molecular weights of the various cellulose samples calculated from a calibration curve. The peak top molecular weight of sample 1 was about 100,000, the peak top molecular weight of sample 2 was 440,000, and the peak top molecular weight of sample 3 was 2,500,000. Panel (B) is a diagram illustrating the patterns of gel filtration obtained by injecting the various samples, and these are data that were used for the preparation of panel (A). The vertical axis represents the signal intensity obtained from the differential refractometer, and the horizontal axis represents the retention time.

2. Measurement of Viscosity of Cellulose Solution

Measurement of the viscosity of a cellulose solution was carried out by using a tuning fork vibration type viscometer (SV-10A) manufactured by A&D Co., Ltd. Each of the cellulose samples was dissolved in DMAc containing 8% LiCl to a concentration of 2.5 mg/mL, and the viscosity was measured at 26° C. Calibration of the viscometer was carried out by using water and a standard solution for viscometer calibration (Nippon Grease Co., Ltd., JS-100). The viscosity values of water and the standard solution at 26° C. were 0.9 mPa·S and 54.0 mPa·S, respectively.

As the results, the viscosity values of 8% LiCl/DMAc (solvent), sample 1 (peak top molecular weight: 100,000), sample 2 (peak top molecular weight: 440,000), and sample 3 (peak top molecular weight: 2,500,000) were 5.3 mPa·S, 7.9 mPa·S, 26.9 mPa·S, and 41.4 mPa·S, respectively.

3. Production of Cellulose Gel Culture Substrate 3-1. Cellulose Gel Culture Substrate Using Sample 1

A cellulose culture substrate at a cellulose concentration of 3% was produced as follows.

Distilled water was added to a commercially available calcium thiocyanate (Kanto Chemical Co., Ltd.), and thus an aqueous solution of calcium thiocyanate was prepared such that the final concentration would be 57% (W/W) or higher. 3 g of the cellulose of sample 1 was added to 100 mL of this calcium thiocyanate solution, and the mixture was stirred for 3 hours or longer at room temperature. The suspension liquid thus obtained was dispensed in an amount of 15 mL into plastic Petri dishes having an internal diameter of 8.4 cm, and then the cellulose was dissolved by heating at 120° C. for one minute. The Petri dishes were left to stand for 2 hours at 4° C., and then were brought to room temperature. Methanol (Wako Pure Chemical Industries, Ltd.) was added thereto in an equal or greater amount, and the Petri dishes were shaken for 2 hours by using a shaker.

After shaking, the Petri dishes were placed in a container filled with tap water, and desalting was carried out while water was caused to flow over. After a period of 2 hours or longer passed, tap water was replaced with distilled water, and the conductivity inside the container where desalting was carried out was measured by using a conductivity meter (Twin Compact Meter, Horiba, Ltd.). At the time point where conductivity reached 10 μS/cm or less, desalting was completed.

The desalted cellulose gel was transferred to containers such as glass Petri dishes or heat-resistant Petri dishes, and the cellulose gel was high pressure steam sterilized at 121° C. for 20 minutes.

Furthermore, a cellulose gel culture substrate at a cellulose concentration of 1% was produced in the same manner as described above, except that the amount of cellulose of sample 1 was changed to 1 g.

3-2. Cellulose Gel Culture Substrate Using Sample 2

Cellulose and water were mixed such that the proportion of water would be 29.7 mL relative to 1 g of the cellulose of sample 2, and the mixture was sufficiently stirred (for 10 minutes or longer) in a beaker. Solid calcium thiocyanate was added thereto such that the final concentration of calcium thiocyanate (tetrahydrate, Kanto Chemical Co., Ltd.) would be 50% (W/W), the total volume of the liquid was adjusted to 100 mL, and the liquid was stirred for 3 hours or longer at room temperature. Thereafter, this solution was stirred for 10 minutes at about 90° C., and the solution was dispensed in an amount of 15 mL each into plastic Petri dishes having an internal diameter of 8.4 cm. Subsequently, the cellulose gel was dissolved by heating for one minute at 120° C. After this heating treatment, the Petri dishes were cooled to 4° C. for 2 hours, ethanol (Junsei Chemical Co., Ltd.) was added thereto in an equal or greater amount at room temperature, and the mixtures were subjected to a shaking treatment for 2 hours at room temperature.

After shaking, the Petri dishes were placed in a container filled with tap water, and desalting was carried out while water was caused to flow over. After a period of 2 hours or longer passed, tap water was replaced with distilled water, and the conductivity inside the container where desalting was carried out was measured by using a conductivity meter (Twin Compact Meter, Horiba, Ltd.). At the time point where conductivity reached 10 μS/cm or less, desalting was completed.

The desalted cellulose gel was transferred to containers such as glass Petri dishes or heat-resistant Petri dishes, and the cellulose gel was high pressure steam sterilized at 121° C. for 20 minutes.

Furthermore, a cellulose gel culture substrate at a cellulose concentration of 0.5% was produced in the same manner as described above, except that the amount of cellulose of sample 2 was changed to 0.5 g.

3-3. Cellulose Gel Culture Substrate Using Sample 3

A cellulose gel culture substrate using sample 3 at a cellulose concentration of 1% was produced according to the same method as that used in the above section 3-2.

The characteristics of the various culture substrates produced as such are presented in FIG. 12.

In FIG. 12, the "density" was calculated by dividing the theoretical value of cellulose content by the volume of the cellulose gel (calculated by measuring the diameter and the thickness with vernier calipers or a rheometer). Furthermore, the "relative volume percentage (%)" was obtained by calculating the relative value (%) of the volume of each cellulose gel with respect to the volume of the cellulose gel of sample 1 (1%) as 100%.

4. External Appearance, Microstructure and Others of Culture Substrate 4-1. External Appearance FIG. 2 presents photographs of various culture substrates produced as described above, taken from above with a camera. Panel (A) illustrates a culture substrate using sample 1 (cellulose concentration: 3%), and panel (B) illustrates a culture substrate using sample 2 (cellulose concentration: 1%).

While the culture substrate using sample 1 was obviously opaque and white in color, the culture substrate using sample 2 was transparent.

4-2. Microstructure

Figure 3:
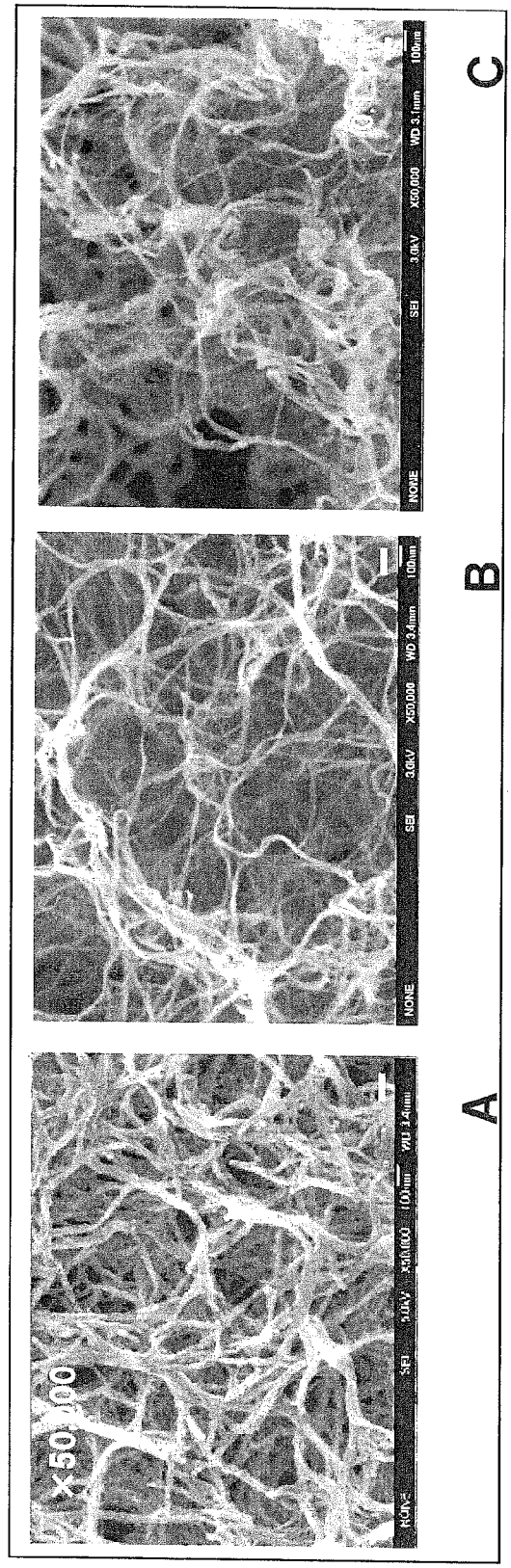
FIG. 3 is diagrams illustrating scanning electron microscopic photographs of various culture substrates (magnification: 50,000 times). Panel (A) illustrates a culture substrate produced by using sample 1 (cellulose concentration: 3%); panel (B) illustrates a culture substrate produced by using sample 2 (cellulose concentration: 1%); and panel (C) illustrates a culture substrate produced by using sample 3 (cellulose concentration: 1%)

The structures of the various culture substrates produced as described above were observed by using a scanning electron microscope (product No. JSM-6700F, manufactured by JEOL, Ltd.) (magnification: 50,000 times). The results are presented in FIG. 3. Panel (A) illustrates a culture substrate produced by using sample 1 (cellulose concentration: 3%), and Panel (B) illustrates a culture substrate produced by using sample 2 (cellulose concentration: 1%). Panel (C) illustrates a culture substrate produced by using sample 3 (cellulose concentration: 1%).

It was confirmed by the electron microscopic photographs that all of the culture substrates formed network structures in which nano-fibrotized cellulose constitutes the skeletal part, and the culture substrates were porous structures having large pores.

4-3. Transparency

In order to further evaluate the transparency of the culture substrates, the cellulose gels in the Petri dishes were scanned by using a spectrophotometer ("Beckman Coulter DU800") in a transmittance measurement (T %) mode over a wavelength range of 300 nm to 800 nm. The thickness of the cellulose gel was about 2 mm (2 mm±0.1 mm) in all cases, and the transmittance of the Petri dish holding the culture substrate was designated as the blank. The transmittances of the cellulose gels were evaluated on the basis of the values measured at a wavelength of 500 nm. For a comparison, measurement was made for a culture substrate using 1% agar (Shimizu Shokuhin Kaisha, Ltd., trade name: "Taiyo-Agar, BMM-5").

The results are presented in FIG. 4. Panel (A) illustrates the transmittances of 1% agar, sample 1 (1% and 3%), and sample 2 (0.5% and 1%). Panel (B) illustrates the transmittances of samples 1 to 3 (all 1%). The transmittances at a wavelength of 500 nm of the culture substrates using sample 2 were 45.8% (SD±4.2) at a cellulose concentration of 1%, and 74.0% (SD±1.3) at a cellulose concentration of 0.5%. The transmittance of sample 2 at a cellulose concentration of 0.5% was comparable to that of agar.

On the other hand, in the culture substrates using sample 1, the transmittances were 12.5% (SD±1.0) at a cellulose concentration of 3%, and 51.4% (SD±4.0) at a cellulose concentration of 1%. In the culture substrate using sample 3, the transmittance was 23.0% (SD±2.0) at a cellulose concentration of 1%.

4-4. Stress

Stress measurement was carried out for the various culture substrates. The measurement of stress was carried out as follows by using Rheometer CR-500DX-SII manufactured by Sun Scientific Co., Ltd. The sample platform was moved at a speed of 1 mm/6 seconds by using a pressure-sensitive shaft having a diameter of 3 mm, and the change in stress during the period ranging from the time point at which the pressure-sensitive shaft was brought into contact with the surface of a cellulose gel (diameter: 6.6 cm to 8.4 cm×thickness 2 mm±0.1 mm) to the time point at which the pressure-sensitive shaft pushed the gel by 1 mm, was monitored (n=3). The maximum stress was measured when the pressure-sensitive shaft was pushed by 1 mm.

Figure 5:
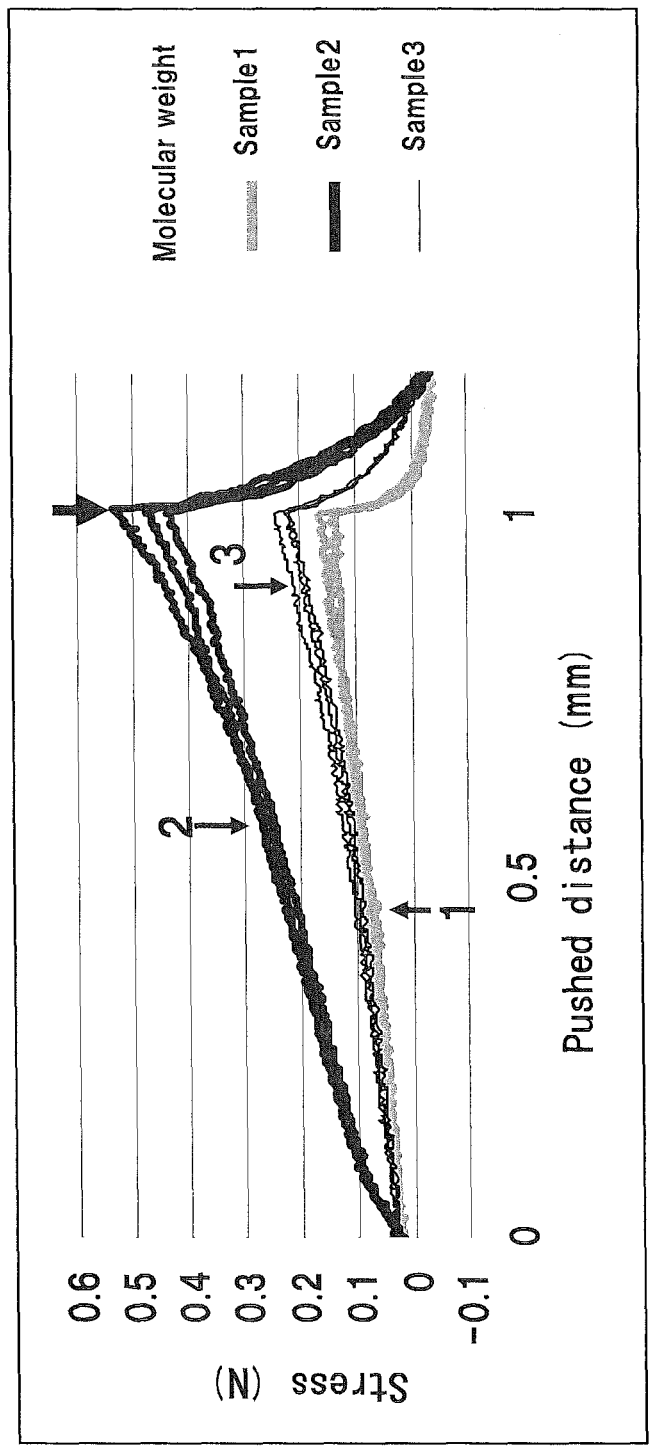
FIG. 5 is a diagram illustrating the stress measured for various culture substrates (cellulose concentration: 1%). The arrow represents the maximum stress value. The bold grey line represents sample 1, the bold black line represents sample 2, and the fine black line represents sample 3.

The measurement results for the culture substrate at a cellulose concentration of 1% are presented in FIG. 5. The maximum stress values (indicated by an arrow) were 0.14±0.08 N in the culture substrate produced by using sample 1, 0.47±0.07 N in the culture substrate produced by using sample 2, and 0.23±0.02 N in the culture substrate produced by using sample 3. Furthermore, the maximum stress values were 0.14±0.00 N in sample 2 at a cellulose concentration of 0.5%, and 0.88±0.04 N in sample 1 at a cellulose concentration of 3%.

It was found that the cellulose gels produced from sample 2 had higher stress values as compared with the cellulose gels produced from sample 1 and sample 3 at the same concentrations.

4-5. Tensile Strength

The tensile strengths of the various culture substrates were measured. Measurement of the tensile strength was carried out as follows by using Rheometer CR-500DX-SII manufactured by Sun Scientific Co., Ltd. The gel samples of the various culture substrates were cut to a dumbbell shape having a width of 1 cm and a length of 3 cm, and thus specimens (thickness: 2 mm±0.1 mm) were prepared. Each specimen was mounted on the analyzer, the sample platform was moved at a speed of 0.42 mm/1 second, and the force required to break the specimen and the pull distance at which the gel broke were measured.

Figure 6:
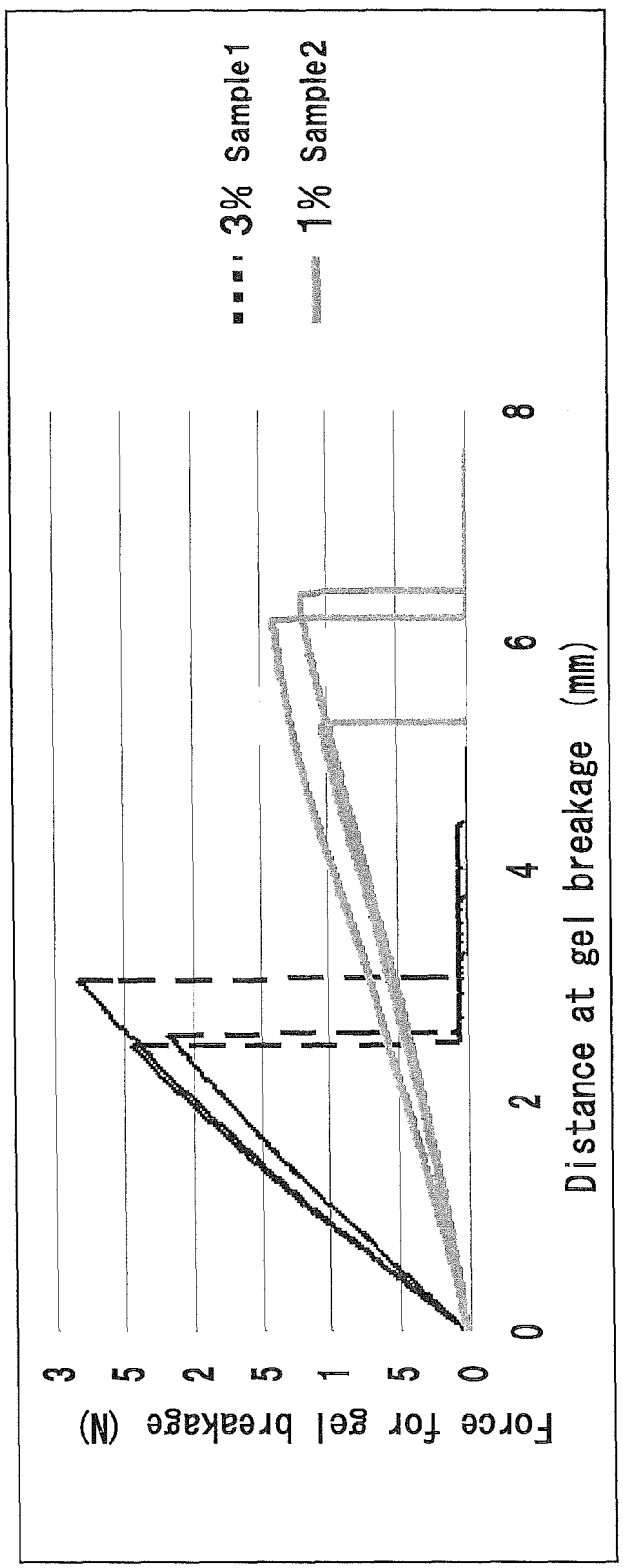
FIG. 6 is a diagram illustrating the tensile strengths of the culture substrates produced by using sample 1 (3%) and sample 2 (1%), respectively (n=3). The dotted line represents sample 1 (3%) and the grey line represents sample 2 (1%)

The results are presented in FIG. 6 and FIG. 13.

The specimen of sample 1 at a cellulose concentration of 1% could not be mounted on the analyzer because of the lack of strength, and measurement could not be made. The culture substrate produced from sample 2 at a cellulose concentration of 1% was such that the force required for breakage was smaller than the culture substrate produced from sample 1 at a cellulose concentration of 3%, but the pull distance was larger by about two times than that of the culture substrate produced from sample 1 at a cellulose concentration of 3%. This implies that the culture substrate produced by using sample 2 is a gel having excellent elasticity.

5. Production of Media and Culture Test for Various Microorganisms

The operations related to microbial culture were all carried out aseptically by using sterilized instruments and solutions.

5-1. Culture Test Using E. Coli

The bacterial strain used was *Escherichia coli* ATCC 25922. As the assay medium, ordinary bouillon medium (Kyokuto Pharmaceutical Industrial Co., Ltd.) was used. To each of the various culture substrates produced as described above, 15 mL of a liquid assay medium at a two-fold concentration that had been high pressure steam sterilized at 121° C. for 20 minutes was added, and the mixture was shaken in a shaker (Taitec Corp.) for 2 hours to infiltrate the liquid medium into the culture substrate. Thus, water in the culture substrate was replaced with a liquid having a medium composition at a one-fold concentration. After 2 hours, the medium remaining in the Petri dish was removed by suction with an aspirator, and the culture substrate was dried in a clean bench for 10 minutes, and then was used as a solid assay medium.

Pre-culture of the bacterium was carried out by aerobic culture in TRI/SOY blood agar medium (sheep) No. 2 (Kyokuto Pharmaceutical Industrial Co., Ltd.) at 37° C. for 18 to 24 hours. Colonies thus obtained were collected and suspended in physiological saline that had been high pressure steam sterilized at 121° C. for 20 minutes, and thus a bacterial fluid at McFarland #0.5 was prepared. This bacterial fluid was further diluted 50,000-fold with sterilized physiological saline. 50 µL each of this bacterial fluid was inoculated into the various solid assay media, and the bacterial fluid was spread uniformly with a Conradi rod. Culture was carried out by aerobic culture at 35° C. for 18 hours. The evaluation of the bacterial strain was carried out by measuring the number of developed colonies (n=9).

Figure 7:
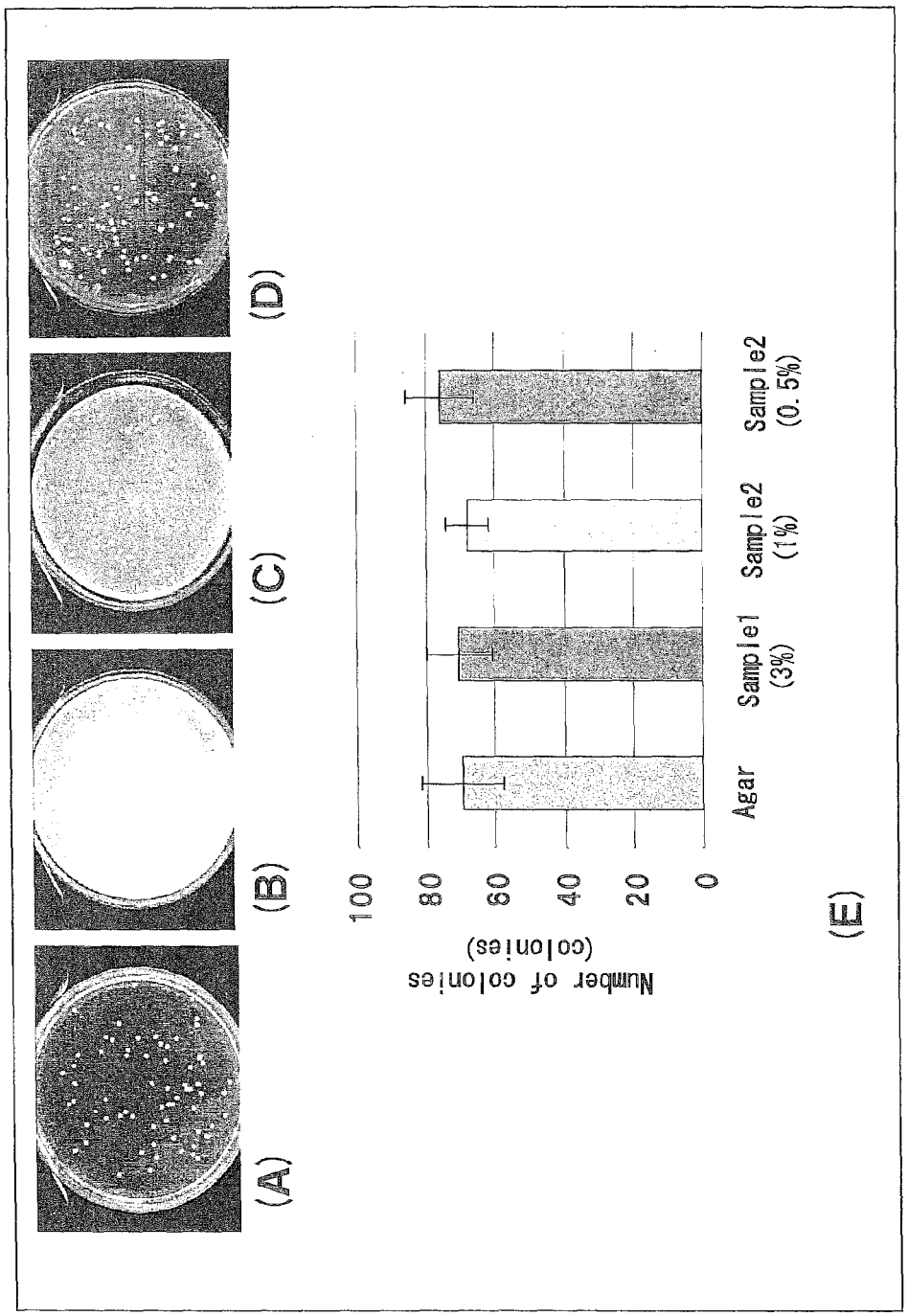
FIG. 7 is diagrams illustrating the results of a test for the growth of *E. coli* on a cellulose gel medium. Panel (A) is a photograph of colonies generated on a medium obtained by using 1% agar as a solidifying agent, panel (B) is a photograph of colonies generated on a medium obtained by using sample 1 (3%) as a solidifying agent, panel (C) is a photograph of colonies generated on a medium obtained by using sample 2 (1%) as a solidifying agent, and panel (D) is a photograph of colonies generated on a medium obtained by using sample 2 (0.5%) as a solidifying agent. Panel (E) is a diagram illustrating the number of colonies generated on each of these media (n=9)

The results are presented in FIG. 7. Panel (A) illustrates a photograph taken from above of colonies produced on the agar medium (1%); panel (B) illustrates a photograph taken from above of colonies produced on the medium of sample 1 (3%); panel (C) illustrates a photograph taken from above of colonies produced on the medium of sample 2 (1%); and panel (D) illustrates a photograph taken from above of colonies produced on the medium of sample 2 (0.5%). The colonies on the medium using sample 2 were easily recognized by visual inspection, similarly to the colonies on the agar medium. Furthermore, *E. coli* exhibited comparable growth on all of the solid media (Panel (E)).

5-2. Culture Test Using B. subtilis

The bacterial strain used was *Bacillus subtilis* ATCC 6633. As the assay medium, ordinary bouillon medium (Kyokuto Pharmaceutical Industrial Co., Ltd.) was used. To each of the various culture substrates produced as described above, 15 mL of a liquid assay medium at a two-fold concentration that had been high pressure steam sterilized at 121° C. for 20 minutes was added, and the mixture was shaken in a shaker (Taitec Corp.) for 2 hours to infiltrate the liquid medium into the culture substrate. Thus, water in the culture substrate was replaced with a liquid having a medium composition at a one-fold concentration. After 2 hours, the medium remaining in the Petri dish was removed by suction with an aspirator, and the culture substrate was dried in a clean bench for 10 minutes, and then was used as a solid assay medium.

Pre-culture of the bacterium was carried out by aerobic culture in TRI/SOY blood agar medium (sheep) No. 2 (Kyokuto Pharmaceutical Industrial Co., Ltd.) at 37° C. for 18 to 24 hours. Colonies thus obtained were collected and suspended in physiological saline that had been high pressure steam sterilized at 121° C. for 20 minutes, and thus a bacterial fluid at McFarland #0.5 was prepared. This bacterial fluid was further diluted 10,000-fold with sterilized physiological saline. 50 µL each of this bacterial fluid was inoculated into the various solid assay media, and the bacterial fluid was spread uniformly with a Conradi rod. Culture was carried out by aerobic culture at 35° C. for 18 hours. The evaluation of the bacterial strain was carried out by measuring the number of developed colonies (n=9).

Figure 8:
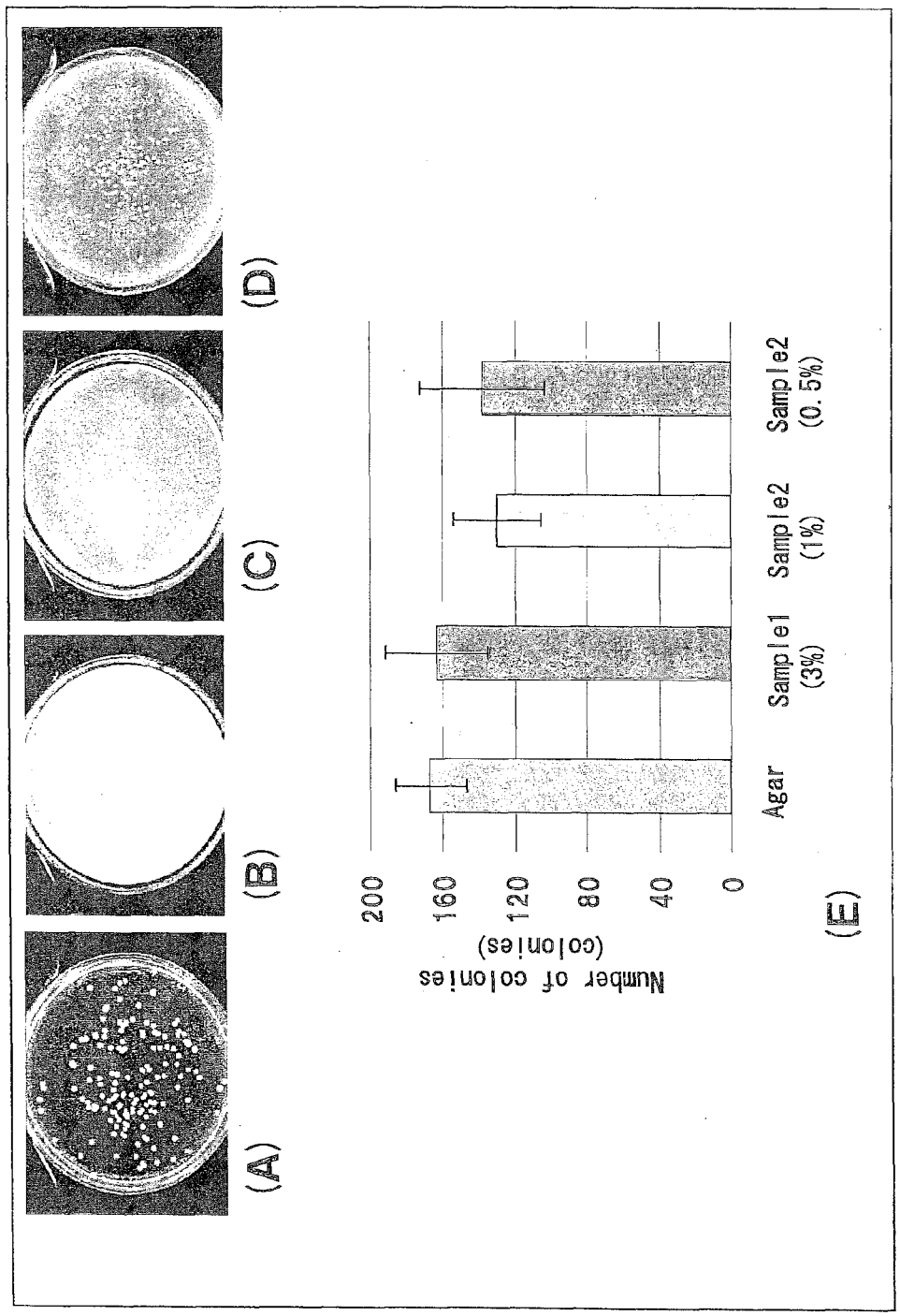
FIG. 8 is diagrams illustrating the results of a test for the growth of a *Bacillus subtilis* on a cellulose gel medium. Panel (A) is a photograph of colonies generated on a medium obtained by using 1% agar as a solidifying agent, panel (B) is a photograph of colonies generated on a medium obtained by using sample 1 (3%) as a solidifying agent, panel (C) is a photograph of colonies generated on a medium obtained by using sample 2 (1%) as a solidifying agent, and panel (D) is a photograph of colonies generated on a medium obtained by using sample 2 (0.5%) as a solidifying agent. Panel (E) is a diagram illustrating the number of colonies generated on each of these media (n=9)

The results are presented in FIG. 8. Panel (A) illustrates a photograph taken from above of colonies produced on the agar medium (1%); panel (B) illustrates a photograph taken from above of colonies produced on the medium of sample 1 (3%); panel (C) illustrates a photograph taken from above of colonies produced on the medium of sample 2 (1%); and panel (D) illustrates a photograph taken from above of colonies produced on the medium of sample 2 (0.5%). The colonies on the medium using sample 2 were easily recognized by visual inspection, similarly to the colonies on the agar medium. Furthermore, *Bacillus subtilis* exhibited comparable growth on all of the solid media (Panel (E)).

5-3. Culture Test Using Yeast

The bacterial strain used was *Candida albicans* ATCC 10231. As the assay medium, Sabouraud glucose medium (Kyokuto Pharmaceutical Industrial Co., Ltd.) was used. To each of the various culture substrates produced as described above, 15 mL of a liquid assay medium at a two-fold concentration that had been high pressure steam sterilized at 121° C. for 20 minutes was added, and the mixture was shaken in a shaker (Taitec Corp.) for 2 hours to infiltrate the liquid medium into the culture substrate. Thus, water in the culture substrate was replaced with a liquid having a medium composition at a one-fold concentration. After 2 hours, the medium remaining in the Petri dish was removed by suction with an aspirator, and the culture substrate was dried in a clean bench for 10 minutes, and then was used as a solid assay medium.

Pre-culture of the yeast was carried out by aerobic culture in Sabouraud agar medium (Kyokuto Pharmaceutical Industrial Co., Ltd.) at 37° C. for 20 to 24 hours. Colonies thus obtained were collected and suspended in physiological saline that had been high pressure steam sterilized at 121° C. for 20 minutes, and thus a yeast fluid at McFarland #0.5 was prepared. This yeast fluid was further diluted 2,500-fold with sterilized physiological saline. 50 µL each of this yeast fluid was inoculated into the various solid assay media, and the yeast fluid was spread uniformly with a Conradi rod. Culture was carried out by aerobic culture at 35° C. for 24 hours. The evaluation of the bacterial strain was carried out by measuring the number of developed colonies (n=9).

Figure 9:
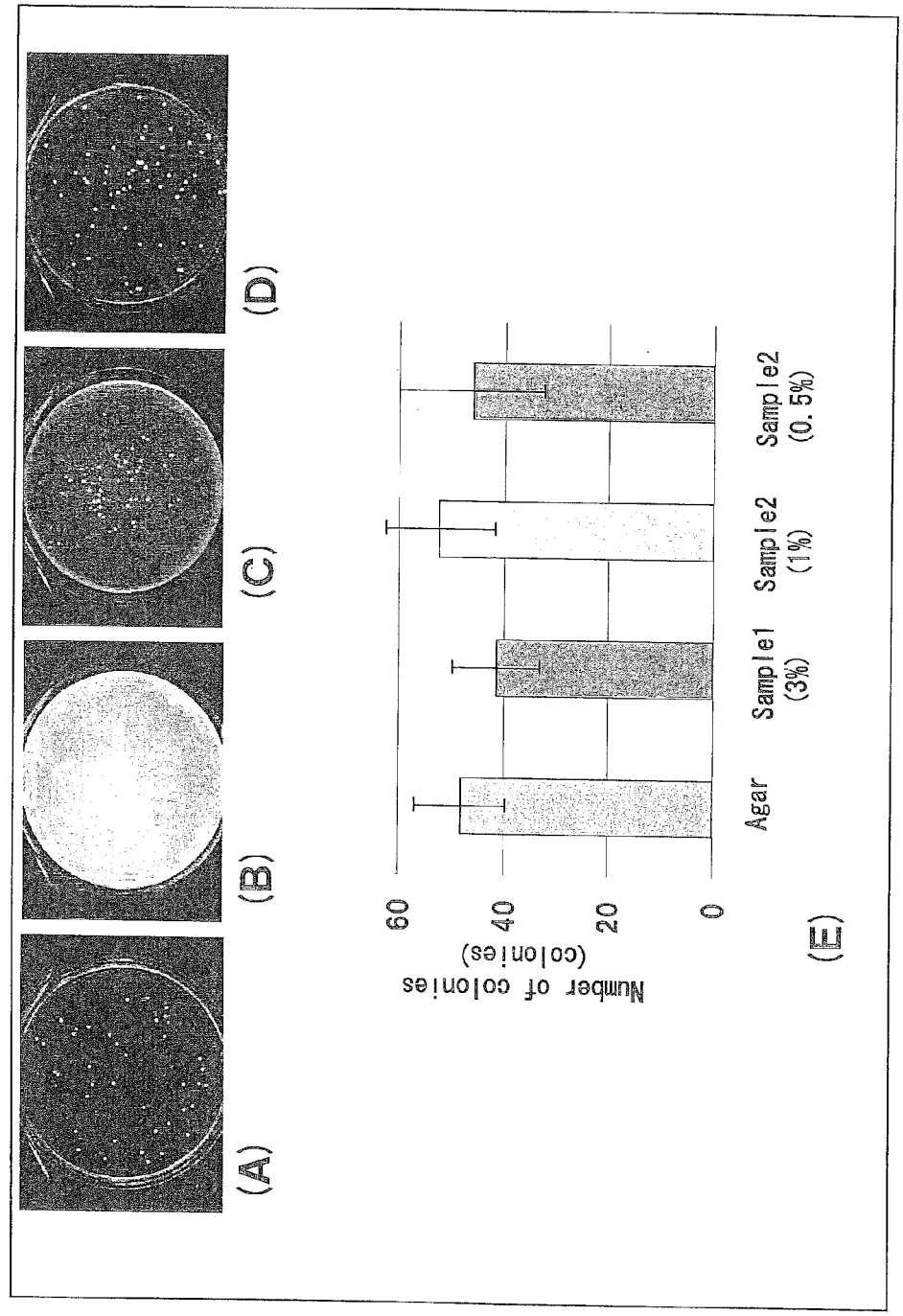
FIG. 9 is diagrams illustrating the results of a test for the growth of a yeast on a cellulose gel medium. Panel (A) is a photograph of colonies generated on a medium obtained by using 1% agar as a solidifying agent, panel (B) is a photograph of colonies generated on a medium obtained by using sample 1 (3%) as a solidifying agent, panel (C) is a photograph of colonies generated on a medium obtained by using sample 2 (1%) as a solidifying agent, and panel (D) is a photograph of colonies generated on a medium obtained by using sample 2 (0.5%) as a solidifying agent. Panel (E) is a diagram illustrating the number of colonies generated on each of these media (n=9)

The results are presented in FIG. 9. Panel (A) illustrates a photograph taken from above of colonies produced on the agar medium (1%); panel (B) illustrates a photograph taken from above of colonies produced on the medium of sample 1 (3%); panel (C) illustrates a photograph taken from above of colonies produced on the medium of sample 2 (1%); and panel (D) illustrates a photograph taken from above of colonies produced on the medium of sample 2 (0.5%). The colonies on the medium using sample 2 were easily recognized by visual inspection, similarly to the colonies on the agar medium. Furthermore, the yeast exhibited comparable growth on all of the solid media (Panel (E)).

5-4. Culture Test Using Cellulase-Producing Bacterium

The bacterial strain used was *Saccharophagus degradans* DSM 17024. As the assay medium, a medium prepared by adding ammonium sulfate (Wako Pure Chemical Industries, Ltd.) to a concentration of 2 mM to Daigo's artificial seawater SP solution (Wako Pure Chemical Industries, Ltd.) at a two-fold concentration, and high pressure steam sterilizing the mixture at 121° C. for 20 minutes, was used. To each of the various culture substrates produced as described above, 15 mL of a liquid assay medium was added, and the mixture was shaken in a shaker (Taitec Corp.) for 2 hours to infiltrate the liquid medium into the culture substrate. Thus, water in the culture substrate was replaced with a liquid having a medium composition at a one-fold concentration. After 2 hours, the medium remaining in the Petri dish was removed by suction with an aspirator, and the culture substrate was dried in a clean bench for 10 minutes, and then was used as a solid assay medium. The culture substrates used were a culture substrate produced by using sample 1 (cellulose concentration: 3%) and a culture substrate produced by using sample 2 (cellulose concentration: 1%).

Preparation of the medium for pre-culture of the bacterium was carried out by the following procedure. 1.87 g of Marine broth (Becton Dickinson and Company) was dissolved in 50 mL of distilled water, and the solution was thoroughly stirred with a magnetic stirrer. Furthermore, a 1% cellobiose (MP Biomedicals LLC) solution in distilled water was separately prepared. Marine broth and the cellobiose solution were high pressure steam sterilized at 121° C. for 20 minutes and cooled to room temperature. Subsequently, Marine broth was filtered through a 0.45-μm membrane filter in a clean bench. 300 μL of the cellobiose solution was added to 3 mL of Marine broth, and the mixture was thoroughly stirred with a vortex mixer.

To 3 mL of the pre-culture medium prepared as described above, 50 μL to 100 μL of a glycerol-preserved bacterial fluid was added dropwise, and the mixture was mixed. The bacterium was pre-cultured by aerobic culture at 30° C. for 20 to 24 hours. The pre-cultured bacterial fluid was diluted to McFarland #0.5 with a Marine broth solution that had been high pressure steam sterilized at 121° C. for 20 minutes, and the bacterial fluid was further diluted 100-fold to 500-fold with the Marine broth solution. 50 μL each of this bacterial fluid was inoculated into the various solid assay media, and the bacterial fluid was spread uniformly with a Conradi rod. Culture was carried out by aerobic culture at 30° C. The diameters of the holes (dissolved holes) formed on each of the media were measured by using an ocular micrometer of a microscope. Five holes were randomly selected from each of the media (n=3), and the average value of those diameters was calculated.

Figure 10:
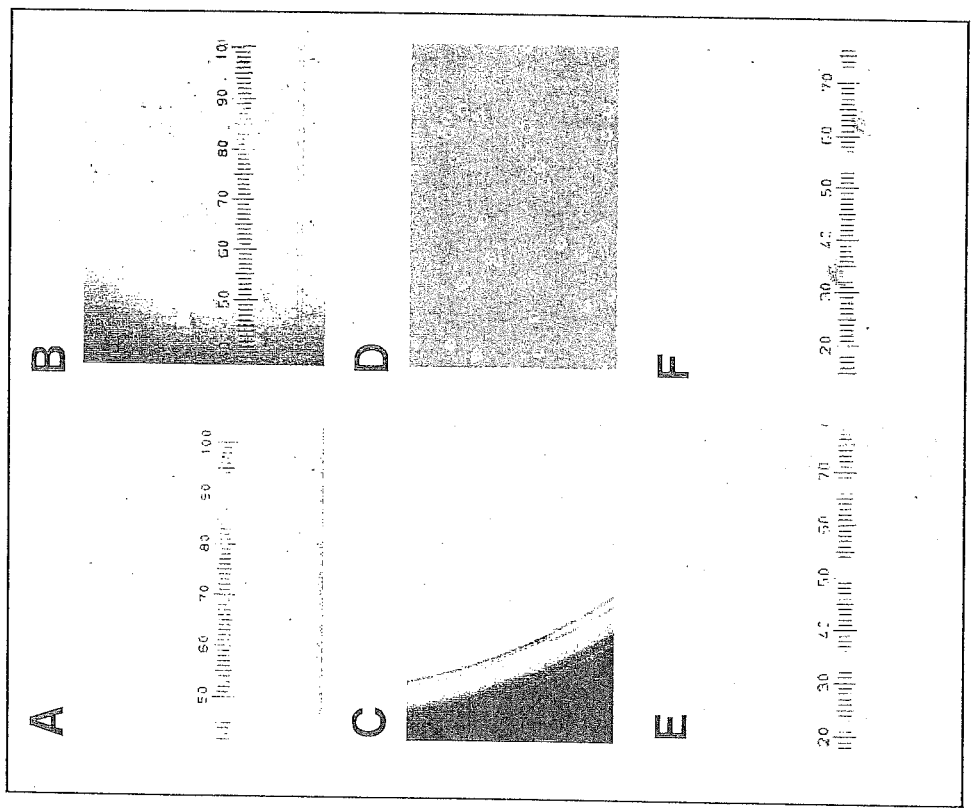
FIG. 10 is diagrams illustrating the photographs of cellulose gel media on which cellulose-decomposing bacteria were grown. Panels (A), (C) and (E) illustrate photographs of colonies (dissolved holes) that were generated on media produced by using sample 1 (3%) as a solidifying agent, and panels (B), (D) and (F) illustrate photographs of colonies (dissolved holes) that were generated on media produced by using sample 2 (1%) as a solidifying agent. The culture time is 48 hours for panels (A) and (B), and 72 hours for panels (C) to (F). One gradation=0.1 mm.

The results are presented in FIG. 10. Panels (A), (C) and (E) illustrate the media of sample 1 (cellulose concentration: 3%); and panels (B), (D) and (F) illustrate the media of sample 2 (cellulose concentration: 1%). Panels (A) and (B) are diagrams illustrating photographs of the medium surfaces after a 48-hour culture, and panels (C) to (F) are diagrams illustrating photographs of the medium surfaces after a 72-hour culture (Panels (A), (B), (E) and (F)).

After the culture for 48 hours, 0.4-mm holes were observed in the medium of sample 2 (cellulose concentration: 1%), but only small holes that were unmeasurable by a microscope (micrometer) were observed in the medium using sample 1. Furthermore, the sizes of the holes were measured after the culture for 72 hours, and the hole size was 0.8 mm in the medium of sample 2, while the hole size was 0.2 mm in the medium of sample 1.

Figure 11:
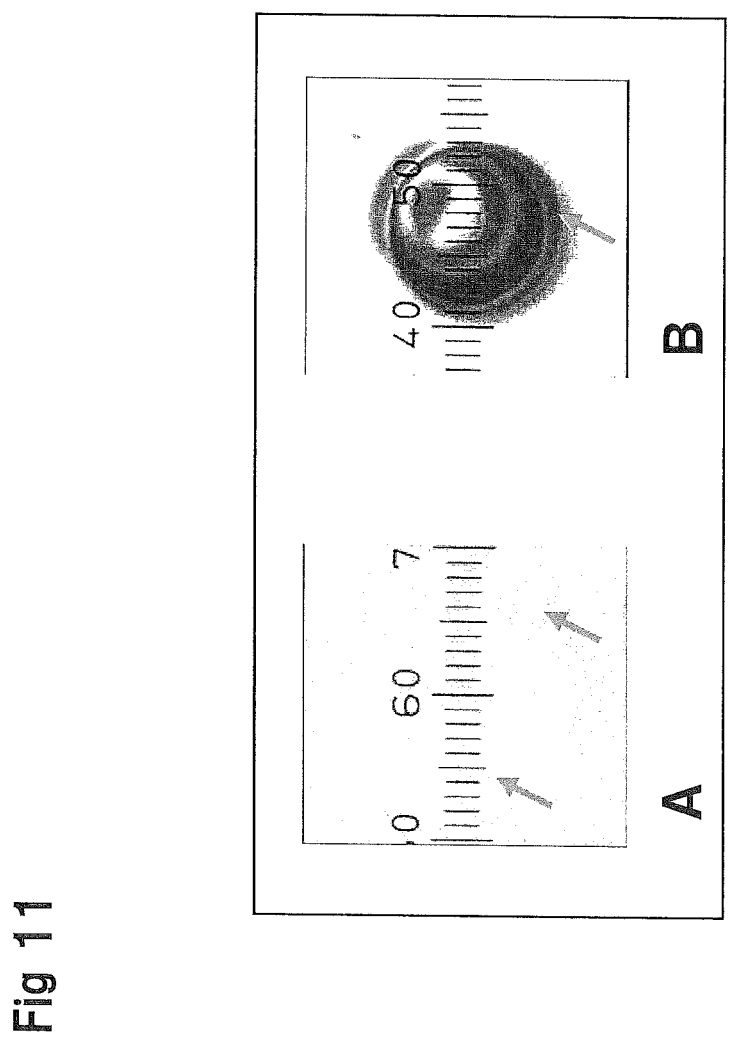
FIG. 11 is diagrams illustrating photographs of cellulose media on which cellulose-decomposing bacteria were grown. Panel (A) illustrates a photograph of colonies generated after 7 days of culture on a medium produced by using sample 1 (3%) as a solidifying agent, and panel (B) illustrates a photograph of colonies generated after 7 days of culture on a medium produced by using sample 2 (1%) as a solidifying agent. The arrows represent the positions of colonies (dissolved holes). One gradation=0.1 mm.

Furthermore, measurements were similarly made after 7 days of culture. The results are presented in FIG. 11. Panel (A) illustrates the medium of sample 1, and panel (B) illustrates the medium of sample 2. The hole size after 7 days was 1.3 mm in the medium of sample 2, while the hole size was 0.4 mm in the medium of sample 1.

Therefore, it was found that in the medium of sample 2 the rate of decomposition of the cellulose media by S. degradans was faster than in the medium of sample 1, and the presence of a decomposing bacterium can be quickly and easily confirmed.

6. Production of Culture Substrates Using Various Cellulose Samples

Cellulose samples with various molecular weights were prepared using sample 2 and sample 3, by referring to Endo Takashi, "Preparation of amorphous cellulose by ball mill treatment" (Cellulose Commun., 13(2): 80-84, 2006).

10 g of the cellulose raw material of sample 2 was placed in a ball mill container (volume: 1 L), and the cellulose raw material was subjected to a ball mill treatment for 0, 5, 18, 30, 43, or 91 hours. Similarly, the cellulose raw material of sample 3 was subjected to a ball mill treatment for 0, 5, 18, 30 or 43 hours.

For the various samples thus treated, the molecular weights were measured by gel filtration as described in section 1. Furthermore, as described in section 2., cellulose solutions were prepared, and the viscosities of the solutions were measured. In addition, culture substrates containing the various samples at a cellulose concentration of 1% were produced according to the method described in section 3., and the transmittance, maximum stress, and density of each of the culture substrates were measured as described in section 4.

The results are respectively summarized in FIG. 14 and FIG. 15.

It was confirmed that in both sample 2 and sample 3, a decrease in the molecular weight and a decrease in viscosity occurred with an increase in the ball mill treatment time, and that there is a positive correlation between the cellulose molecular weight and the viscosity.

In all of the culture substrates produced by using sample 2 and sample 3 respectively as solidifying agents, the transmittance at a wavelength of 500 nm increased with a decrease in the molecular weight and a decrease in viscosity (Tables 3 and 4). In regard to sample 3, it was already known that when a culture substrate was produced by using untreated cellulose, the gel would shrink (Table 1). The cellulose density increases as a result of this shrinkage, and the light transmittance inevitably decreases. However, culture substrates produced by using celluloses obtained after a ball mill treatment were such that as the treatment time increased, the relative volume percentage (%) became close to 100%. That is, it is speculated that since the cellulose density of the cellulose gel decreased with an increase in the treatment time, and accordingly, shrinkage of the culture substrate was also suppressed, the transmittance of the culture substrate increased. The transmittance reached the maximum when the ball mill treatment time was 30 hours.

On the other hand, when the cellulose of sample 3 that had been treated for 43 hours was used, the density decreased, but the transmittance also decreased, so that transparency was deteriorated. This phenomenon was also recognized in the cellulose of sample 2 that had been treated for 91 hours (FIG. 15).

In regard to the culture substrates produced by using sample 2 as a solidifying agent, it was found that the molecular weight and the viscosity decreased with a treatment for 5 hours to 43 hours, and that in this extent of a decrease in the molecular weight (or decrease in viscosity), the properties (transmittance, stress and density) of the culture substrates thus produced were not affected. However, in the cellulose of sample 2 that had been treated for 91 hours, the properties of the culture substrates thus produced became very brittle.

This patent application is based on Japanese patent application JP 2010-244327 filed Oct. 29, 2010, and the entirety of the subject matters described in the specification and claims of JP 2010-244327 is incorporated herein by reference.

The invention claimed is:

1. A culture substrate formed of a cellulose gel containing a cellulose as a medium solidifying component and water,
wherein the cellulose having a viscosity of 12 mPa·S to 35 mPa·S as measured at 26° C. with a solution prepared by dissolving the cellulose in a dimethylacetamide solution that contains 8% (W/V) lithium chloride, wherein a concentration of the cellulose in the dimethylacetamide solution is 2.5 mg/mL,
wherein the culture substrate having a concentration of the cellulose at 0.1% to 1.8%, and
wherein a maximum stress value of the culture substrate having a concentration of the cellulose at 1% is 0.47±0.07 N.

2. The culture substrate according to claim 1, wherein the light transmittance of the cellulose gel having a thickness of 2 mm at a wavelength of 500 nm is 25% or greater.

3. The culture substrate according to claim 1, wherein the peak top molecular weight of the cellulose obtainable by gel filtration is 115,000 to 1,100,000.

4. The culture substrate according to claim 1, wherein the culture substrate is disposed in a container.

5. A solid medium formed of the culture substrate according to claim 1, wherein the cellulose gel includes a nutrient component.

6. The culture substrate according to claim 2, wherein the peak top molecular weight of the cellulose obtainable by gel filtration is 115,000 to 1,100,000.

7. The culture substrate according to claim 2, wherein the culture substrate is disposed in a container.

8. The culture substrate according to claim 3, wherein the culture substrate is disposed in a container.

9. A solid medium formed of the culture substrate according to claim 2, wherein the cellulose gel includes a nutrient component.

10. A solid medium formed of the culture substrate according to claim 3, wherein the cellulose gel includes a nutrient component.

11. A solid medium formed of the culture substrate according to claim 4, wherein the cellulose gel includes a nutrient component.

12. A method for producing a culture substrate, the method comprising
dispersing in water cellulose having a viscosity of 12 mPa·S to 35 mPa·S as measured at 26° C. with a solution prepared by dissolving the cellulose in a dimethylacetamide solution that contains 8% (W/V) lithium chloride, wherein a concentration of the cellulose in the dimethylacetamide solution is 2.5 mg/mL,
adding a solid thiocyanate,
subsequently heating and dissolving the cellulose to form a solution, and
solidifying the solution by lowering the temperature to produce the culture substrate,
wherein the culture substrate having a concentration of the cellulose at 0.1% to 1.8%,
and wherein a maximum stress value of the culture substrate having a concentration of the cellulose at 1% is 0.47±0.07 N.

13. A method for assaying cellulase production by a test microorganism or cellulase activity of a test specimen, the method comprising
bringing a solid medium into contact with the test microorganism or the test specimen,
wherein the solid medium comprising a nutrient and a culture substrate formed of a cellulose gel,
wherein the culture substrate comprises water and a cellulose as a medium solidifying component,
wherein the cellulose having a viscosity of 12 mPa·S to 35 mPa·S as measured at 26° C. with a solution prepared by dissolving the cellulose in a dimethylacetamide solution that contains 8% (W/V) lithium chloride,
wherein a concentration of the cellulose in the dimethylacetamide solution is 2.5 mg/mL,
wherein the culture substrate having a concentration of the cellulose at 0.1% to 1.8%,
wherein a maximum stress value of the culture substrate having a concentration of the cellulose at 1% is 0.47±0.07 N, and
determining presence or absence, or a degree of dissolution of the cellulose gel.

14. The method of claim 13, wherein the light transmittance of the cellulose gel having a thickness of 2 mm at a wavelength of 500 nm is 25% or greater.

15. The method of claim 13, wherein the peak top molecular weight of the cellulose obtainable by gel filtration is 115,000 to 1,100,000.

16. The method of claim 13, wherein the solid medium is disposed in a container.

* * * * *